United States Patent [19]

Kume et al.

[11] Patent Number: 5,017,213
[45] Date of Patent: May 21, 1991

[54] 1-PHENYLPYRROLES

[75] Inventors: Toyohiko Kume; Toshio Goto; Atsumi Kamochi; Akihiko Yanagi; Hiroshi Miyauchi; Tadao Asami, all of Tokyo, Japan

[73] Assignee: Nihon Tokushu Noyaku Seizo K. K., Tokyo, Japan

[21] Appl. No.: 376,719

[22] Filed: Jul. 7, 1989

[30] Foreign Application Priority Data

Jul. 18, 1988 [JP] Japan ................................ 63-177042
Oct. 22, 1988 [JP] Japan ................................ 63-266662

[51] Int. Cl.$^5$ .................... C07D 401/10; A01N 43/40
[52] U.S. Cl. ............................................ 71/95; 71/94;
71/72; 548/563; 548/406; 548/516; 548/131;
548/203; 548/128; 548/125; 548/247;
548/266.2; 548/266.4; 548/264.2; 546/272;
546/4 M
[58] Field of Search .............. 548/563, 406, 516, 247,
548/265, 131, 203, 128, 125; 71/95, 92, 94;
546/272; 544/333

[56] References Cited

FOREIGN PATENT DOCUMENTS 304528 1/1973 Austria .
3735641 4/1988 Fed. Rep. of Germany .

OTHER PUBLICATIONS

Chemical Abstracts, vol. 68, Jun. 3, 1968, No. 23, 105181s.
Chemical Abstracts, vol. 84, Jun. 21, 1976, No. 25, p. 584.
Chemical Abstracts, vol. 92, May 12, 1980, No. 19, p. 587.
Journal of Chemical Society, vol. 14, 1970, pp. 2563-2567.
Journal of Heterocyclic Chemistry, vol. 9, No. 4, Aug. 1972, pp. 1413-1417.
Tetrahedron, vol. 23, No. 11, pp. 4469-4479, 1967.
J. Chem., Soc., 1970, No. 18, pp. 2563-2567.
J. Heterocycl. Chem., vol. 9, No. 6, pp. 1413-1417, 1972.
Khim. Farm. Ah., vol. 10, No. 9, pp. 55-60, 1976.
Yutaka et al., CA 82:125271p.

Primary Examiner—Jane T. Fan
Attorney, Agent, or Firm—Sprung Horn Kramer & Woods

[57] ABSTRACT

Herbicidal 1-phenylpyrroles of the formula

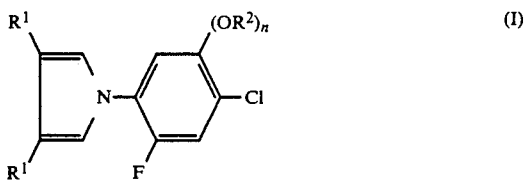

wherein
each $R^1$ represents methyl or together form a tetramethylene group,
$R^2$ represents hydrogen, $C_{1-6}$ alkyl, cyclopropylmethyl, $C_{1-4}$ alkoxy-$C_{1-2}$ alkyl, $C_{1-4}$ alkylthio-$C_{1-2}$ alkyl, $C_{1-4}$ alkylsulfinyl-$C_{1-2}$ alkyl, $C_{1-4}$ alkylsulfonyl-$C_{1-2}$ alkyl, benzyl or phenylethyl which are optionally substituted by halogen, $C_{3-4}$ alkenyl, $C_{3-4}$ alkynyl, $C_{3-4}$ haloalkenyl, $C_{2-3}$ cyanoalkyl or carbmoylmethyl, thiocarbamoylmethyl, trimethylsilylmethyl, $CH_2COOR^3$,

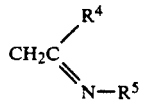

or a $C_{1-2}$ alkyl group which is connected with an optionally substituted 5-6 membered heterocyclic group, wherein
$R^3$ represents $C_{1-6}$ alkyl or $C_{5-6}$ cycloalkyl,
$R^4$ represents hydrogen, methyl, ethyl or cyclopropyl,
$R^5$ represents $OR^6$ or $N(CH_3)_2$, in which
$R^6$ represents hydrogen, $C_{1-5}$ alkyl, allyl, propargyl or benzyl, and
n represents 0 to 1.

11 Claims, No Drawings

1-PHENYLPYRROLES

The present invention relates to novel 1-phenylpyrroles, to processes for their preparation and to their use as herbicides.

Certain 1-phenylpyrroles have already been known (see Tetrahedron vol. 23, No. 11, pp. 4467–4479, 1967, J. Chem., Soc., 1970, No. 18, pp. 2563–2567, J. Heterocycl. Chem., vol. 9, No. 6, pp. 1413–1417, 1972 and Khim. Farm. Zh., vol. 10, No. 9, pp 55–60, 1976) but no disclosure was made of herbicidal function in the references.

There have now been found novel 1-phenylpyrroles of the formula (I)

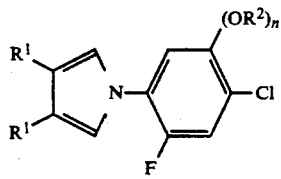

wherein
$R^1$ represents methyl or a tetramethylene group formed by two $R^1$s being connected together,
$R^2$ represents hydrogen, $C_{1-6}$alkyl, cyclopropylmethyl, $C_{1-4}$alkoxy-$C_{1-2}$alkyl, $C_{1-4}$alkylthio-$C_{1-2}$alkyl, $C_{1-4}$alkylsulfinyl-$C_{1-2}$alkyl, $C_{1-4}$alkylsulfonyl-$C_{1-2}$alkyl, or $R^2$ represents benzyl or phenylethyl which are optionally substituted by halogen, or $R^2$ furthermore represents, $C_{3-4}$alkenyl, $C_{3-4}$haloalkenyl, $C_{3-4}$alkynyl, $C_{2-3}$cyanoalkyl, carbamoylmethyl, thiocarbamoylmethyl, trimethylsilylmethyl, $CH_2COOR^3$,

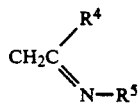

or a $C_{1-2}$ alkyl group which is connected with an optionally substitutable 5 or 6 membered heterocyclic group, wherein the five-membered heterocyclic group preferably contains one nitrogen atom and one or two further heteroatoms selected from nitrogen, sulphur and oxygen and wherein the six-membered heterocyclic group preferably contains one or two nitrogen atoms, wherein
$R^3$ represents $C_{1-6}$alkyl or $C_{5-6}$cycloalkyl,
$R^4$ represents hydrogen, methyl, ethyl or cyclopropyl,
$R^5$ represents $OR^6$ or $N(CH_3)_2$, in which
$R^6$ represents hydrogen, $C_{1-5}$alkyl, allyl, propargyl or benzyl, and
n represents 0 or 1.

The compounds of the formula (I) can be obtained by a process in which,
(a) compounds of the formula (II)

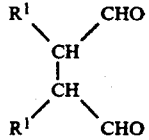

wherein $R^1$ represents the same substituents as mentioned above, are reacted with compounds of the formula (III)

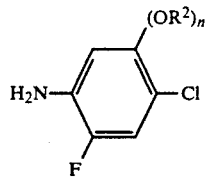

wherein $R^2$ and n represent the same substituents as mentioned above,
in the presence of inert solvents, or
(b) compounds of the formula (IV)

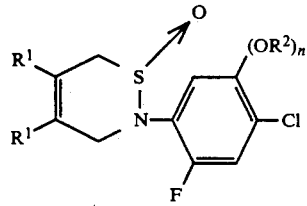

wherein $R^1$, $R^2$ and n represents the same substituents as mentioned above,
are subjected to alkali treatment, in the presence of inert solvents, or
(c) in the case where $R^2$ represents other definitions than hydrogen, compounds of the formula (V)

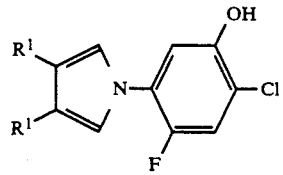

wherein $R^1$ represents the same substituents as mentioned above,
are reacted with compounds of the formula (VI)

wherein
$R^{2-1}$ represents the same substituent as $R^2$ but without hydrogen,
M represents halogen, methane sulfonyloxy, tosyloxy or $R^{2-1}$—$OSO_2$—O, in which $R^{2-1}$ represents the same as mentioned above,
in the presence of inert solvents and if appropriate, in the presence of a base.

The novel-1-phenylpyrroles, according to the invention exhibit powerful herbicidal properties.

According to the study of the present inventors, it has been found surprisingly that, as compared, for example, with known compounds such as those disclosed in the above-mentioned publications, the present 1-phenylpyrroles represented by the general formula (I) exhibit substantially a highly distinguished herbicidal activity.

Among the 1-phenylpyrroles according to the invention of the formula (I), preferred compounds are those in which
$R^1$ represents methyl or a tetramethylene group formed by two $R^1$s being connected together,
$R^2$ represents hydrogen, $C_{1-4}$alkyl, cyclopropylmethyl, $C_{1-2}$alkoxy-$C_{1-2}$alkyl, $C_{1-2}$alkylthio-$C_{1-2}$alkyl, $C_{1-}$ $_{2}$alkylsulfinyl-methyl, $C_{1-2}$alkylsulfonyl-methyl, benzyl, $C_3$-alkenyl, $C_3$-haloalkenyl, propargyl, cyanomethyl, or a methyl group connected with a five-membered heterocyclic group or a six-membered aromatic heterocyclic group each comprising at least one nitrogen atom, preferably one nitrogen atom and one or two further heteroatoms selected from nitrogen, sulphur and oxygen regarding the five-membered ring and preferably one or two nitrogen atoms regarding the six-membered ring, wherein said five- and six-membered ring may be substituted with $C_{1-2}$alkyl or $C_{1-2}$alkoxy, and n represents 0 or 1.

Very particularly preferred 1-phenylpyrroles of the formula (I) are those in which $R^1$ represents methyl or a tetramethylene group formed by two $R^1$s being connected together, $R^2$ represents n-propyl, iso-propyl, n-, iso-, sec. or tert.-butyl, cyclopropylmethyl, methoxymethyl, ethoxymethyl, methylthiomethyl, ethylthiomethyl, benzyl, allyl, 2-chloro-allyl, propargyl, cyanomethyl or a methyl group connected with a five-membered heterocyclic group comprising one or two nitrogen atoms and either an oxygen or sulfur atom, or a methyl group connected with a six-membered aromatic heterocyclic group comprising one or two nitrogen atoms, preferably pyridine or pyrimidine, wherein said five- and six-membered rings may be substituted with methyl or methoxy groups, and n represents 1.

In the above-mentioned definitions of $R^2$ and in the definition $R^{2-1}$ mentioned below the five-membered or six-membered heterocyclic ring substituents may include, as preferable examples, triazole, especially 1,2,4-triazole, oxadiazole, especially 1,2,5-oxadiazole, thiadiazole, especially 1,2,5-thiadiazole, thiazole, pyridine, pyrimidine, etc.

Specifically, the following compounds may be mentioned:

2-(4-chloro-2-fluoro-5-propargyloxyphenyl)-4,5,6,7-tetrahydroisobenzindole, 3,4-dimethyl-1-(4-chloro-2-fluoro-5-propargyloxyphenyl)-pyrrole, 2-(5-allyloxy-4-chloro-2-fluorophenyl)-4,5,6,7-tetrahydroisobenzindole, 2-[4-chloro-2-fluoro-5-(pyridin-2-yl-methoxyphenyl]-4,5,6,7-tetrahydroisobenzindole, and 2-[4-chloro-2-fluoro-5-(isoxazol-3-yl-methoxy)phenyl]-4,5,6,7-tetrahydroisobenzindole.

If as starting materials in the process (a) there are employed, for instance, 1,2-cyclohexane dicarboxyaldehyde and 4-chloro-2-fluoro-5-propargyloxyaniline, the reaction can be expressed by the following scheme:

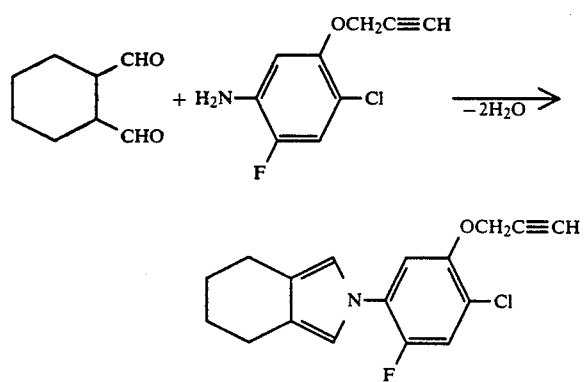

If as starting materials in the process (b) there are employed, for example, 4,5-dimethyl-2-(4-chloro-2-fluoro-5-propargyloxyphenyl)-2,3-dihydro-6H-1,2-thiazine-1-oxide and potassium hydroxide, the reaction can be expressed by the following scheme:

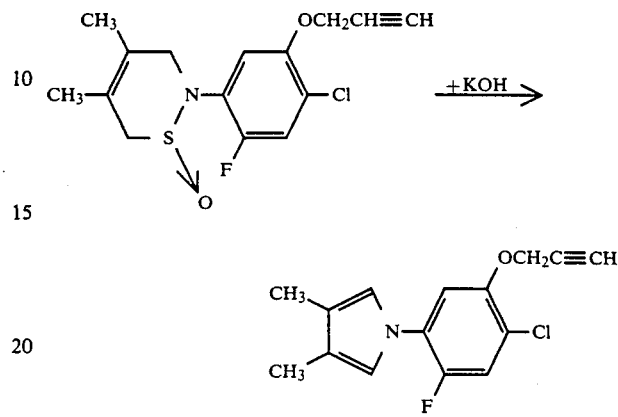

If as starting material in the process (c) there is employed, for instance, 3,4-dimethyl-1-(4-chloro-2-fluoro-5-hydroxyphenyl)pyrrole and bromoacetonitrile, the reaction may be expressed by the following scheme:

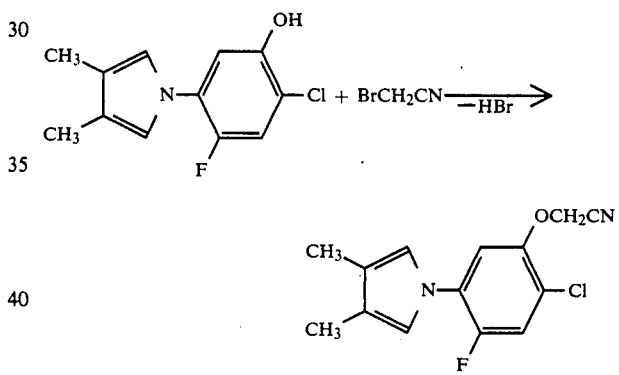

Referring to compounds of the formula (II) employed as starting materials in the process (a), the symbol $R^1$ in this formula has the same meaning as stated before. Furthermore, in the formula (II), the symbol $R^1$ preferably has the same preferred meaning as stated before.

The compounds of the formula (II) are known in themselves, and specifically 1,2-cyclohexane dicarboxyaldehyde can generally be prepared according to the process disclosed by Ann. vol. 560, page 1, 1948 wherein cyclooctatetraene is converted to 7,8-dihydroxybicyclo[4,2,0] octane through a four-stage reaction, which is then reacted with lead tetracetate at the final reaction stage.

Further, the compound (II) mentioned above can be prepared by the process that was disclosed by J. Am. Chem. Soc., Div. Polymer Chem. Preprints, vol. 5, No. 1, pages 210-215, 1964, wherein 1,2-cyclohexane dicarboxylic acid is converted to the corresponding dicarboxylic acid chloride that is in turn reacted with N-methylaniline to form the corresponding bis-(N-methylanilide) which is then reduced with lithium aluminum hydride or according to the process disclosed by J. Am. Chem. Soc. vol. 74, pages 3014-3018, 1952, wherein 4-cyclohexane-1,2-dicarboxyaldehyde is formed from 2,5-dimethoxy-2,5-dihydrofuran and butadiene, which is then catalytically reduced.

Further, 1,2-cyclohexane dicarboxyaldehyde can be prepared by the following process, besides the above-mentioned three known processes, in which (d) the compound 1,2-cyclohexanedimethanol

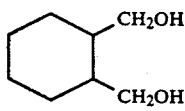

is oxidized in the presence of inert solvents.

The above-mentioned 1,2-cyclohexanedimethanol can be easily obtained by reducing 1,2-cyclohexanedicarboxylic anhydride, according to a known process.

As for the oxidizing agent employed in process (d), use may be made, for example, of dimethylsulfoxide-oxalic dichloride (J. Org. Chem. vol. 44, page 4148, 1979), pyridinium dichromate (Tetr. Letter, page 399, 1979), pyridinium chlorochromate (Tetr. Letter, page 2647, 1975), manganese dioxide, oxygen, lead tetraacetate, copper oxide, ammonium cerium (IV) nitrate (Synthesis, page 347, 1973), paradium (II) salt, dimethylsulfoxide-dicyclohexylcarbodimide (J. Am. Chem. Soc. vol. 85, page 3027, 1963) and so on.

Compared with any known process, the above-mentioned process (d) requires the minimum number of steps as well as very simple procedures.

Regarding the starting materials represented by the general formula (III) employed as a reaction partner in the process (a), the substituents are those as defined under the above-mentioned symbol $R^2$.

In the general formula (III), the symbols $R^2$ and n have the same preferable meanings as mentioned before.

The compounds represented by the general formula (III) are known compounds as disclosed by EP-OS Nos. 61714 and 69855, and Japanese Patent Laid-Open No. 74639/1988.

Examples of the compounds represented by the general formula (III) include:
4-chloro-2-fluoro-5-propoxyaniline,
4-chloro-5-cyclopropylmethoxy-2-fluoroaniline,
4-chloro-2-fluoro-5-methoxymethoxyaniline,
4-chloro-2-fluoro-5-methylthiomethoxyaniline,
4-chloro-5-ethoxymethoxy-2-fluoroaniline,
4-chloro-5-ethylthiomethoxy-2-fluoroaniline,
5-benzyloxy-4-chloro-2-fluoroaniline,
5-allyloxy-4-chloro-2-fluoroaniline,
4-chloro-5-(2-chloroallyloxy)-2-fluoroaniline,
4-chloro-2-fluoro-5-propargyloxyaniline,
4-chloro-5-cyanomethoxy-2-fluoroaniline,
4-chloro-2-fluoro-5-(isoxazol-3-yl-methoxy)aniline,
4-chloro-2-fluoro-5-(4-methyl-1,2,5-oxaziazol-3-yl-methoxy)aniline,
4-chloro-2-fluoro-5-(thiazol-4-yl-methoxy)aniline,
4-chloro-2-fluoro-5-(pyridin-2-yl-methoxy)aniline, and so on.

Regarding the starting materials represented by the general formula (IV) employed in the process (b) mentioned above, the substituents are those as defined under the above-mentioned symbols $R^1$, $R^2$ and n.

In the general formula (IV), the symbols $R^1$, $R^2$ and n have the same preferable meanings as mentioned before.

The compounds represented by the general formula (IV) can be obtained by the following process (e) wherein compounds having the general formula

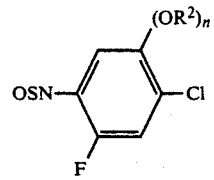

wherein $R^2$ has the same meaning as mentioned above, are reacted with 2,3-dimethyl-1,3-butadiene.

The above-mentioned compounds represented by the general formula (VII) can be obtained by the following process (f), wherein the compounds having the above-mentioned general formula (III) are reacted with thionyl chloride.

The above-mentioned processes (e) and (f) will be concretely described in the examples, hereinafter, which may generally be carried out according to the process that is described in Collection Czechoslov. Chem. Communications, vol. 19, pages 282–296, 1954 and the same publication, vol. 19, pages 275–280, 1954.

The compounds represented by the general formula (V) employed in the above-mentioned process (c), are included in the compounds represented by the general formula (I) of the present invention. Therefore, they can be prepared according to the above-mentioned processes (a) and (b).

Regarding the compounds represented by the general formula (VI) employed in the above-mentioned process (c), the substituents are likewise those as defined for the above-mentioned symbols $R^{2-1}$ and M and preferably $R^{2-1}$ represents a $C_{1-4}$alkyl, cyclopropylmethyl, $C_{1-2}$alkoxy-$C_{1-2}$alkyl, $C_{1-2}$alkylthio-$C_{1-2}$alkyl, benzyl, $C_3$-alkenyl, $C_3$-haloalkenyl, propargyl or cyanomethyl, group, or a methyl group connected with a five-membered heterocyclic group or a six-membered aromatic heterocyclic group each comprising at least one nitrogen atom, preferably one nitrogen atom and one or two further hetero atoms selected from nitrogen, sulphur and oxygen regarding the five-membered ring and preferably one or two nitrogen atoms regarding the six-membered ring, wherein said five- and six-membered ring each may be substituted with $C_{1-2}$-alkyl or $C_{1-2}$-alkoxy, M represents chloro, bromo, iodo, methanesulfonyloxy, tosyloxy or $R^{2-1}$—$OSO_2$—$O$— and $R^{2-1}$ represents the same substituents as defined preferably for the above-mentioned symbol $R^{2-1}$.

Examples include:
methyl iodide, dimethyl sulfate, ethyl iodide, isopropyl iodide, propyl iodide, sec-butyl iodide, n-butyl iodide, cyclopropylmethyl bromide, chloromethyl methylether, chloromethyl ethylether, chloromethyl methyl sulfide, chloromethyl ethyl sulfide, benzyl chloride, 2-fluorobenzyl chloride, 4-fluorobenzyl chloride, 2-chlorobenzyl chloride, 4-chlorobenzyl chloride, 3-bromo-1-propene, 3-bromo-2-methyl-1-propene, 2,3-dichloro-1-propene, 1,3-dichloro-1-propene, 1,2,3-trichloro-1-propene, 1,1,2,3-tetrachloro-1-propene, 3-bromo-1-butene, 3-bromo-1-propyne, 3-bromo-1-butyne, chloroacetonitrile, 2-bromopropionitrile, bromoacetonitrile, 2-(chloromethyl)pyridine, 2-(chloromethyl)pyrazine, 1-(chloromethyl)-1H-1,2,4-triazole, 5-(chloromethyl)-1-methyl-1H-1,2,4-triazole, 3-(chloromethyl)isoxazole, 3-(chloromethyl)-5-methyl- 1,2,4-oxadiazole, 5-(chloroethyl)-3-methyl-1,2,4-oxadiazole, 3-(bromomethyl)-4-methyl-1,2,5-oxadiazole, 2-(chloromethyl)-5-methyl-1,3,4-oxadiazole, 4-(chloromethyl)thiazole, 3-(chloromethyl)-5-methoxy-1,2,4-thiadiazole, 3-(chloromethyl)-5-ethoxy-1,2,4-thiadiazole, 3-(bromomethyl)-1,2,5-thiadiazole, 2-(chloromethyl)-5-methyl-1,3,4-thiadiazole, etc.

As appropriate diluents for carrying out the process (a), any kind of inert organic solvents can be mentioned.

As examples of such solvents, use may be made preferably of aliphatic hydrocarbons such as, for example, petroleum ether, dichloromethane, chloroform, carbon tetrachloride; aromatic hydrocarbons such as benzene, toluene, xylene, chlorobenzene, and further; ethers such as, for example, dimethoxyethane, 1,4-dioxane, tetrahydrofuran; alcohols such as methanol, ethanol, ethylcellosolve, ethylene glycol; and organic acids such as acetic acid.

The reaction temperature of the process (a) may vary in a fairly wide range. In general, the reaction is carried out at a temperature of about 50° to about 200° C., preferably a temperature of about 80° to about 150° C. It is preferred to carry out the reaction under normal pressure, although a higher or lower pressure can also be used.

In conducting the process (a), about 1.3 moles of the compounds of the formula (III) may, for instance, be employed per mole of the compounds of the formula (II) in the presence of an inert solvent and, as will be stated in the following examples, refluxing while being heated so that the desired compounds of the formula (I) can be obtained.

When the process (b) is carried out, it is advantageous to use a diluent, including alcohols such as methanol and ethanol.

The process (b) may be conducted at a temperature of about 50° to about 150° C.

It is preferred to carry out the reaction under normal pressure, although a higher or lower pressure can also be used.

In conducting the process (c), use may be made, as appropriate diluents, of inert solvents.

As examples of such solvents, use may be made of water, alcohols such as methanol; ethanol; nitriles such as acetonitrile, propionitrile; ethers such as tetrahydrofuran, 1,4-dioxane; hydrocarbons such as petroleum ether, chloroform, carbon tetrachloride, benzene, toluene, xylene, chlorobenzene; amides such as N,N-dimethyl-formamide, tetramethylurea, N-methyl-2-pyrrolidone, 1,3-dimethyl-5-imidazolidone.

Further, the process (c) may also be carried out in the presence of phase transfer catalysts such as, for example, trimethylbenzyl ammonium chloride, tetrabutyl ammonium bromide, etc.

The process (c) may also be carried out in the presence of a base such as for example, selected from the group consisting of sodium carbonate, potassium carbonate, potassium hydroxide, sodium hydroxide, sodium methoxide, sodium ethoxide, potassium tert. butoxide, sodium hydride, etc.

The reaction temperature of the process (c) may vary in a fairly wide range. In general, the reaction is carried out at a temperature of about 10° to about 150° C., preferably a temperature of about 40° to about 100° C.

It is preferred to carry out the reaction under normal pressure, although a higher or lower pressure can also be used.

In conducting the process (c), from about 1 to 1.2 moles of the compounds of the general formula (VI) may, for instance, be employed per mole of the compounds of the general formula (V) while the reaction is carried out in the presence of a base and inert solvent to obtain the desired compound having the general formula (I).

The active compounds according to the invention can be used as defoliants, desiccants, agents for destroying broad-leaved palnts and, especially, as weedkillers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be emplyed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the slective combating of weeds in annual cultures.

The active compounds can be converted into the customary formulations, such as solutions, emulsions, wet-table powders, suspensions, powders, foams, pastes, granules, aerosols, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid solvents diluents or carriers, there are suitable in the main, aromatic hydrocarbons, such as xylene, toluene or alkyl napthalenes, chlorinated aromatic or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethyl-sulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulation.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese boron, copper, cobalt, molybdenum and zinc.

The formulations in general contain from 0.1 to 95 percent by weight of active compound, preferably from 0.5 to 90 percent by weight.

The active compounds according to the invention, as such or in the form of their formulations, can also be used, for combating weeds, as mixtures with known herbicides, finished formulations or tank mixes being possible.

Mixtures with other known active compounds, such as herbicides, fungicides, insecticides, acaricides, nematicides, bird repellents, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants.

They can also be incorporated into the soil before sowing. They are used, in particular, after emergence of the plants.

The amount of active compound used can vary within a substantial range. It depends essentially on the nature of the desired effect. In general, the amounts used are between 0.0001 and 3 kg of active compound per hectare of soil surface, preferably between 0.001 and 2 kg per ha.

The preparation and use of the active compounds according to the invention can be seen from the following examples.

PREPARATIVE EXAMPLES

Example 1

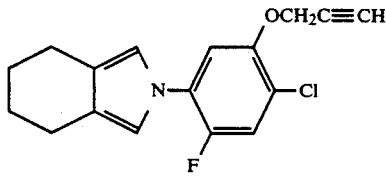

1.4 g of 1,2-cyclohexanedicarboxyaldehyde and 2.2 g of 4-chloro-2-fluoro-5-propargyloxyaniline were added to 50 ml of xylene, and then heated under reflux for 1 hour. The xylene was distilled off from the solution under reduced pressure, and the resulting residue was purified through a silica-gel column (hexane:ethylacetate=9:1) to obtain 2.2 g of the desired 2-(4-chloro-2-fluoro-5-propargyloxyphenyl)-4,5,6,7-tetrahydroisobenzindole. $n_D^{20}$ 1.5938.

Example 2

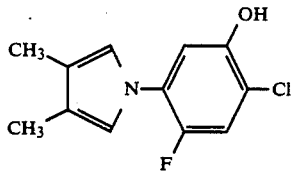

To a solution of 4.39 g of 4-chloro-2-fluoro-5-methoxycarbonyloxy-aniline dissolved in 40 ml of toluene were added 2.86 g of thionyl chloride, followed by one-hour refluxing under heating. After the completion of reaction, the excessive amount of thionyl chloride and the solvent were distilled off under reduced pressure from the reaction product. The resulting residue was dissolved in 40 ml of toluene, to which were added 2.46 g of 2,3-dimethyl-1,3-butadiene followed by heating under reflux for five hours. The solvent was distilled off under reduced pressure and the residue was dissolved in 60 ml of ethanol, while the non-dissolved portion was removed by filtration. The filtrate was added to about 100 ml of ethanol solution containing 3.7 g of potassium hydroxide, followed by one-hour refluxing. After completion of the reaction, the solvent was distilled off under reduced pressure. A small amount of water was added to the reaction product which, after having been neutralized with hydrochloric acid, was extracted twice with dichloromethane (50 ml each time), dried with anhydrous magnesium sulfate, freed from the solvent by distillation at reduced pressure and purified by silica-gel column chromatography to obtain 2.42 g of 3,4-dimethyl-1-(4-chloro-2-fluoro-5-hydroxyphenyl)-pyrrole having a m.p. in the range of 84° to 85° C.

Example 3

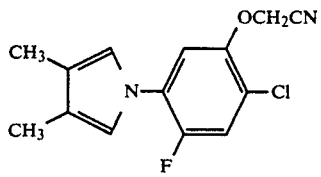

0.96 g of 3,4-dimethyl-1-(4-chloro-2-fluoro-5-hydroxyphenyl)-pyrrole, 0.58 g of bromoacetonitrile and 0.55 g of powdery anhydrous potassium carbonate in 40 ml of acetonitrile were heated for four hours. After completion of the reaction, the solvent was distilled off from the reaction mixture under reduced pressure. A small amount of water was added to the residue that was in turn extracted twice with dichloromethane (30 ml each time).

After drying with anhydrous postassium carbonate, the solvent was distilled off from the extract under reduced pressure. The residue was purified through silica-gel column chromatography to obtain 0.88 g of the desired 3,4-dimethyl-1-(4-chloro-5-cyanomethoxy-2-fluorophenyl)-pyrrole. $n_D^{20}$ 1.5792.

Example 4

Synthesis of a Starting Material

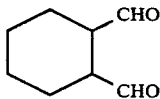

To a solution of 20 ml of oxalic chloride in 300 ml of dichloromethane was added dropwise a solution of 34 ml of dimethyl sulfoxide in 100 ml of dichloromethane at a temperature of $-70°$ C. under stirring, while the temperature of the reaction solution being kept below $-55°$ C. After the dropwise addition had been completed, the reaction solution was stirred for five minutes and, thereafter, a solution of 14.4 g of cis-1,2-cyclohexanedimethanol in 100 ml of dichloromethane was added thereto within a five minute period. After 15 minutes of stirring, 140 ml of triethylamine was added to the solution which was allowed to stand until it returned to room temperature. Then, 300 ml of water was added to the reaction solution, followed by removal of the dichloromethane layer therefrom; after the aqueous layer was washed with 200 ml of dichloromethane, the resulting organic layers were combined and washed with saturated sodium chloride solution. The organic layer was dried with anhydrous sodium sulfate and concentrated under reduced pressure. The resulting residue was distilled under reduced pressure and, by collecting the resulting fractions boiling in the range of from 85° to 90° C. at 5 mmHg, 11.8 g of the desired 1,2-cyclohexanedicarboxyaldehyde was obtained.

Background Example

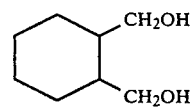

63 g of anhydrous cis-1,2-cyclohexanedicarboxylic acid was dissolved in 200 ml of dried ether and the solution was added dropwise to an ice-cooled suspension of 29 g of lithium aluminum hydride in 1000 ml of dried ether. After completion of the dropwise addition, the solution was heated under reflux for 30 minutes, following return to room temperature, 50 ml of water was added thereto, followed by filtration. The filter cake was washed twice with tetrahydrofuran (200 ml each time). The ethereal filtrate and the tetrahydrofuran washings were combined, dried over anhydrous sodium sulfate, and then concentrated under reduced pressure. The resiude was distilled under reduced pressure and fractions boiling at 122° to 125° C. (0.7 mmHg) were collected to obtain 53 g of pure cis-1,2-cyclohexanedimethanol.

According to the same procedures as employed in the foregoing Examples 1 to 3, the following compounds having the general formula (I) of the present invention were obtained, which are shown in Table 1 together with the compounds which were obtained according to the Examples 1 to 3:

TABLE 1

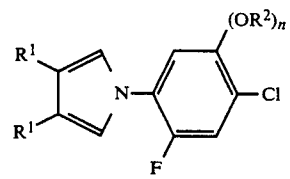

| Compound No. | R¹ | (OR²)ₙ | melting point/°C. or $n_D^{20}$ |
|---|---|---|---|
| 1 | —(CH₂)₄— | H | $n_D^{50}$ 1.5851 |
| 2 | CH₃ | OH | mp. 84–85° C. |
| 3 | —(CH₂)₄— | OH | |
| 4 | —(CH₂)₄— | OCH₃ | |
| 5 | —(CH₂)₄— | OC₂H₅ | |
| 6 | CH₃ | OC₃H₇-iso | $n_D^{20}$ 1.5600 |
| 7 | —(CH₂)₄— | OC₃H₇-iso | |
| 8 | CH₃ | OC₃H₇-n | oil |
| 9 | —(CH₂)₄— | OC₃H₇-n | oil |
| 10 | —(CH₂)₄— | OC₄H₉-sec | |
| 11 | —(CH₂)₄— | OC₄H₉-n | |

TABLE 1-continued

[Structure: pyrrole with R¹ substituents at 3,4-positions, N-linked to benzene ring bearing (OR²)ₙ, Cl, and F substituents]

| Compound No. | R¹ | (OR²)ₙ | melting point/°C. or $n_D^{20}$ |
|---|---|---|---|
| 12 | $-(CH_2)_4-$ | $O-CH_2-\triangleleft$ (cyclopropyl) | |
| 13 | $-(CH_2)_4-$ | $OC_5H_{11}$-n | |
| 14 | $-(CH_2)_4-$ | $OC_6H_{13}$-n | |
| 15 | $-(CH_2)_4-$ | $OCH_2-C_6H_5$ | |
| 16 | $-(CH_2)_4-$ | $OCH_2-C_6H_4-Cl$ | |
| 17 | $-(CH_2)_4-$ | $OCH_2CH=CH_2$ | |
| 18 | $-(CH_2)_4-$ | $OCH_2CCl=CH_2$ | |
| 19 | $-(CH_2)_4-$ | $OCH_2CH=CHCl$ | |
| 20 | $-(CH_2)_4-$ | $OCH_2CCl=CHCl$ | |
| 21 | $-(CH_2)_4-$ | $OCH_2CCl=CCl_2$ | |
| 22 | $CH_3$ | $OCH_2C\equiv CH$ | sticky oil |
| 23 | $-(CH_2)_4-$ | $OCH_2C\equiv CH$ | $n_D^{20}$ 1.5938 |
| 24 | $-(CH_2)_4-$ | $OCH_2OCH_3$ | |
| 25 | $-(CH_2)_4-$ | $OCH_2OC_2H_5$ | |
| 26 | $-(CH_2)_4-$ | $OCH_2SCH_3$ | |
| 27 | $-(CH_2)_4-$ | $OCH_2SC_2H_5$ | |
| 28 | $CH_3$ | $OCH_2CN$ | $n_D^{20}$ 1.5792 |
| 29 | $-(CH_2)_4-$ | $OCH_2CN$ | oil |
| 30 | $-(CH_2)_4-$ | $OCH(CH_3)CN$ | |
| 31 | $CH_3$ | $OCH_2$-(2-pyridyl) | mp. 125–126.5° C. |
| 32 | $-(CH_2)_4-$ | $OCH_2$-(2-pyridyl) | mp. 110–113° C. |
| 33 | $CH_3$ | $OCH_2$-(pyrazinyl) | |

TABLE 1-continued

[Structure: pyrrole with R¹ substituents at 3,4-positions, N-linked to phenyl ring bearing (OR²)ₙ, Cl, and F substituents]

| Compound No. | R¹ | (OR²)ₙ | melting point/°C. or $n_D^{20}$ |
|---|---|---|---|
| 34 | —(CH₂)₄— | OCH₂-(pyrazine) | |
| 35 | CH₃ | OCH₂—N(1,2,4-triazole) | |
| 36 | —(CH₂)₄— | OCH₂—N(1,2,4-triazole) | |
| 37 | CH₃ | OCH₂-(isoxazole) | mp. 91–97° C. |
| 38 | —(CH₂)₄— | OCH₂-(isoxazole) | mp. 90–100° C. |
| 39 | CH₃ | OCH₂-(5-methyl-1,2,4-oxadiazole) | |
| 40 | O(CH₂)₄— | OCH₂-(5-methyl-1,2,4-oxadiazole) | |
| 41 | CH₃ | OCH₂-(3-methyl-1,2,4-oxadiazole) | mp. 68–71° C. |
| 42 | —(CH₂)₄— | OCH₂-(3-methyl-1,2,4-oxadiazole) | |
| 43 | CH₃ | OCH₂-(4-methylisoxazole) | |
| 44 | —(CH₂)₄— | OCH₂-(4-methyl-1,2,5-oxadiazole) | |

TABLE 1-continued

Structure: pyrrole (with R¹ substituents at 3,4 positions) N-linked to a benzene ring bearing (OR²)ₙ, Cl, and F substituents.

| Compound No. | R¹ | (OR²)ₙ | melting point/°C. or $n_D^{20}$ |
|---|---|---|---|
| 45 | CH₃ | OCH₂-(thiazole) | |
| 46 | —(CH₂)₄— | OCH₂-(thiazole) | |
| 47 | CH₃ | OCH₂-(1,2,4-thiadiazole-OCH₃) | |
| 48 | —(CH₂)₄— | OCH₂-(1,2,4-thiadiazole-OCH₃) | |
| 49 | CH₃ | OCH₂-(1,2,4-thiadiazole-OC₂H₅) | |
| 50 | —(CH₂)₄— | OCH₂-(1,2,4-thiadiazole-OC₂H₅) | |
| 51 | CH₃ | OCH₂-(1,2,5-thiadiazole) | |
| 52 | —(CH₂)₄— | OCH₂-(1,2,5-thiadiazole) | |
| 53 | CH₃ | OCH₂-(thiadiazole-CH₃) | |
| 54 | —(CH₂)₄— | OCH₂-(thiadiazole-CH₃) | |
| 55 | —(CH₂)₄— | OCH₂S(O)₂—CH₃ | mp. 105–114° C. |
| 56 | —(CH₂)₄— | OCH₂C(O)NH₂ | |

TABLE 1-continued

[Structure: pyrrole-N-phenyl with R¹ substituents, (OR²)ₙ, Cl, and F substituents]

| Compound No. | R¹ | (OR²)ₙ | melting point/°C. or $n_D^{20}$ |
|---|---|---|---|
| 57 | —(CH₂)₄— | OCH₂C(=S)NH₂ | |
| 58 | —(CH₂)₄— | OCH₂Si(CH₃)₃ | |
| 59 | —(CH₂)₄— | OCH₂COOC₂H₅ | oil |
| 60 | —(CH₂)₄— | OCH₂COO-cyclopentyl | |
| 61 | —(CH₂)₄— | OCH₂C(=O)CH₃ | |
| 62 | —(CH₂)₄— | OCH₂CH=N—OCH₃ | |
| 63 | —(CH₂)₄— | OCH₂C(=N—OH)CH₃ | |
| 64 | —(CH₂)₄— | OCH₂C(=N—OH)CH₃ | |
| 65 | —(CH₂)₄— | OCH₂C(=N—OCH₂CH=CH₂)CH₃ | |
| 66 | —(CH₂)₄— | OCH₂C(=N—OCH₂—phenyl)CH₃ | |
| 67 | —(CH₂)₄— | OCH₂S(=O)—CH₃ | |
| 68 | —(CH₂)₄— | O—CH(CH₃)—C≡CH | |

Biotest Example

Control compounds

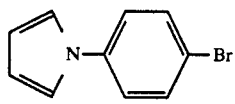

(disclosed in J. Chem. Soc., No. 18, pages 2563–2567, 1970)

E-1

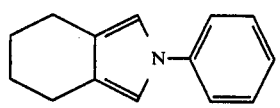

E-2

(disclosed in Khim. Farm. Zh., vol. 10 (No. 9), pages 55–60, 1976)

Example 5

Test on weeds in a flooded paddy by water surface application:

Preparation of an Active Compound Formulation

Carrier: 5 parts by weight of acetone

Emulsifier: 1 part by weight of benzyloxy polyglycol ether

A formulation of an active compound was obtained as an emulsifiable concentrate by mixing 1 part by weight of the active compound with the above-mentioned amounts of the carrier and the emulsifying agent. A predetermined amount of the formulation was diluted with water.

Testing Method

Paddy soil was filled in pots (1/2,000 are: 25×20×9 cm), and rice seedlings (variety: "Nihonbare") in the 2.5-leaf stage (15 cm tall) were transplanted at two places per pot each as a stock of three seedlings. Seeds of barnyard grass (*Echinochloa oryzicola* Vasing.), umbrella plant (*Cyperus difformis* L.), monochoria (*Monochoria vaginalis*, and annual broadleaved weeds false pimpernel (*Lindernia pyxidaria* L.), *Rotala indica*, American waterwort (*Elatine triandra*), red stem (*Ammannia multiflora* Roxburgh) and *Dopatrium junceum* Hamilton were sown and the pots were maintained wet. Two days later, the pots were flooded to a depth of about 2 to 3 cm. Five days after the transplantation of the seedlings, the compound of this invention, in the form of an emulsifiable concentrate as prepared above, was applied to the water surface by a pippette in a predetermined amount. Thereafter, the flooded condition of about 3 cm was maintained, and four weeks after the chemical treatment, the herbicidal effect and the phytotoxicity to rice were evaluated and rated on the scale of 0 to 5 as follows:

Herbicidal effect (evaluated by a weed killing ratio based on a non-treated lot):
5: at least 95% (withered)
4: at least 80% but less than 95%
3: at least 50% but less than 80%
2: at least 30% but less than 50%
1: at least 10% but less than 30%
0: less than 10% (no effect)

Phytotoxicity to crop (evaluated based on a non-treated lot):
5: at least 90% (fatal injury)
4: at least 50% but less than 90%
3: at least 30% but less than 50%
2: at least 10% but less than 30%
1: more than 0 but less than 10%
0: 0% (no phytotoxicity)

The test results are shown in Table 2.

TABLE 2

| Active compound No. | Amount of active compound (kg/ha) | Herbicidal effect on weeds | | | | Phytotoxic effect on rice plants |
|---|---|---|---|---|---|---|
| | | Barnyard grass | Umbrella plant | Monochoria | Annual broadleaved grass | |
| 22 | 0.5 | 5 | 5 | 5 | 5 | 0 |
|  | 0.25 | 4 | 5 | 5 | 5 | 0 |
| 23 | 0.5 | 5 | 5 | 5 | 5 | 1 |
|  | 0.25 | 5 | 5 | 5 | 5 | 0 |
| (Known compound) | | | | | | |
| E-1 | 1.0 | 0 | 0 | 0 | 0 | 0 |
| E-2 | 1.0 | 0 | 0 | 0 | 0 | 0 |

Example 6

Pre-Emergence Soil Treatment Test Against Upland Weeds

In a greenhouse, soybean seeds were sown in 500 cm² pots filled with upland farm soil, and soil containing seeds of Digitaria (*Digitaria sanguinalis*), livid amaranth (*Amaranthus lividus* L.) and goose-foot (*Chenopodium album* L.) was put over the soil in the pots in a depth of 1 cm.

One day after the sowing, a test chemical in a predetermined concentration, prepared as in Example 5, was uniformly sprayed over the surface layer of the soil in each of the test pots.

Four weeks after the spraying, the herbicidal effect and the phytotoxicity to crops were examined on the same standards as in Example 5. The results are shown in Table 3.

TABLE 3

| Active compound No. | Amount of active compound (kg/ha) | Herbicidal effect on weeds | | | Phytotoxic effect on soy bean plants |
|---|---|---|---|---|---|
| | | Digitaria | Livid amaranth | Goose-foot | |
| 6 | 1.0 | 3 | 5 | 5 | 0 |
| 22 | 0.5 | 4 | 5 | 5 | 0 |
|  | 0.25 | 3 | 5 | 5 | 0 |
| 23 | 0.5 | 5 | 5 | 5 | 0 |
|  | 0.25 | 4 | 5 | 5 | 0 |
| (Known compound) | | | | | |
| E-1 | 1.0 | 0 | 0 | 0 | 0 |
| E-2 | 1.0 | 0 | 0 | 0 | 0 |

Example 7

Herbicidal Test by Foliage Application on Upland Weeds

In a greenhouse, corn seeds were sown in 500 cm² pots filled with upland farm soil, and soil containing seeds of Digitaria (*Digitaria sanguinalis*), livid amaranth (*Amaranthus lividus* L.) and goosefoot (*Chenopodium album* L.) was put over the soil in the pots in a depth of 1 cm.

After sowing, the plants were grown for 14 days and a test chemical in a predetermined concentration, prepared as in Example 5, was uniformly sprayed over the test plants in each of the test pots.

Four weeks after the spraying, the herbicidal effect and the phytotoxicity to crops were examined on the same standards as in Example 5. The results are shown in Table 4.

TABLE 4

| Active compound No. | Amount of active compound (kg/ha) | Herbicidal effect on weeds | | | Phyto-toxicity on corn plants |
|---|---|---|---|---|---|
| | | Digi-taria | Livid amaranth | Goose-foot | |
| 22 | 1.0 | 5 | 5 | 5 | 1 |
|  | 0.5 | 4 | 5 | 4 | 0 |
| 23 | 0.5 | 4 | 5 | 5 | 1 |
|  | 0.25 | 3 | 5 | 4 | 0 |
| (Known compound) | | | | | |
| E-1 | 1.0 | 0 | 0 | 0 | 0 |
| E-2 | 1.0 | 0 | 0 | 0 | 0 |

It will be appreciated that the instant specification and claims are set forth by way of illustration and not limitation, and that various modifications and changes may be made without departing from the spirit and scope of the present invention.

What is claimed is:

1. A 1-phenylpyrrole of the formula

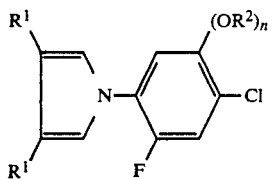

wherein each $R^1$ represents methyl or together form a tetramethylene group, $R^2$ represents hydrogen, $C_{1-6}$ alkyl, cyclopropylmethyl, $C_{1-4}$ alkoxy-$C_{1-2}$ alkyl, $C_{1-4}$ alkylthio-$C_{1-2}$ alkyl, $C_{1-4}$ alkylsulfinyl-$C_{1-2}$ alkyl, $C_{1-4}$ alkylsulfonyl-$C_{1-2}$ alkyl, or $R^2$ represents benzyl or phenylethyl which are optionally substituted by halogen, or $R^2$ furthermore represents $C_{3-4}$ alkenyl, $C_{3-4}$ alkynyl, $C_{3-4}$ haloalkenyl, $C_{2-3}$ cyanoalkyl or carbamoylmethyl, thiocarbamoylmethyl, trimethylsilylmethyl, $CH_2COOR^3$,

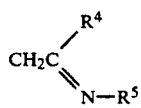

or a $C_{1-2}$ alkyl group which is connected with a heterocyclic ring consisting of triazole, oxadiazole, thiadiazole, thiazole, pyridine and pyrimidine wherein said heterocyclic ring may be substituted with $C_{1-2}$ alkyl or $C_{1-2}$ alkoxy $R^3$ represents $C_{1-6}$ alkyl or $C_{5-6}$ cycloalkyl, $R^4$ represents hydrogen, methyl, ethyl or cyclopropyl, $R^5$ represents $OR^6$ or $N(CH_3)_2$, in which $R^6$ represents hydrogen, $C_{1-5}$ alkyl, allyl, propargyl or benzyl, and n represents 0 or 1.

2. A compound according to claim 1, wherein $R^2$ represents hydrogen, $C_{1-4}$ alkyl, cyclopropylmethyl, $C_{1-2}$ alkoxy-$C_{1-2}$ alkyl, $C_{1-2}$ alkylthio-$C_{1-2}$ alkyl, $C_{1-2}$ alkylsulfinyl-methyl, $C_{1-2}$ alkylsulfonyl-methyl, benzyl, $C_3$-alkenyl, $C_3$-haloalkenyl, propargyl, cyanomethyl, or a methyl group connected with a heterocyclic ring consisting of triazole, oxadiazole, thiadiazole, thiazole, pyridine and pyrimidine, wherein said heterocyclic ring may be substituted with $C_{1-2}$ alkyl or $C_{1-2}$ alkoxy, and n represents 0 or 1.

3. A compound according to claim 1, wherein $R^2$ represents n-propyl, iso-propyl, n-, iso-, sec- or tert.-butyl, cyclopropylmethyl, methoxymethyl, ethoxymethyl, methylthiomethyl, ethylthiomethyl, benzyl, allyl, 2-chloro-allyl, propargyl, cyanomethyl, or a methyl group connected with a heterocyclic ring consisting of triazole, oxadiazole, thiadiazole, thiazole, pyridine and pyrimidine wherein said heterocyclic ring may be substituted with methyl or methoxy, and n represents 1.

4. A compound according to claim 1, wherein such compound is 2-(4-chloro-2-fluoro-5-propargyloxyphenyl)-4,5,6,7-tetrahydroisobenzindole of the formula

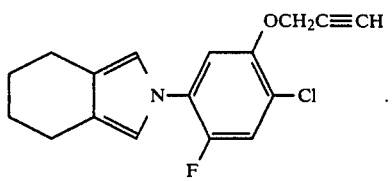

5. A compound according to claim 1, wherein such compound is 3,4-dimethyl-1-(4-chloro-2-fluoro-5-propargyloxyphenyl)-pyrrole of the formula:

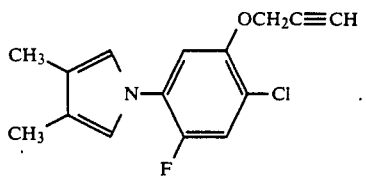

6. A compound according to claim 1, wherein such compound is 2-(5-allyloxy-4-chloro-2-fluorophenyl)-4,5,6,7-tetrahydroisobenzindole of the formula:

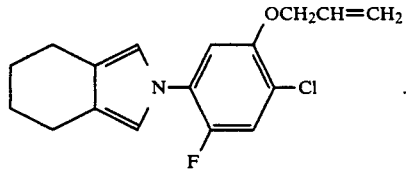

7. A compound according to claim 1, wherein such compound is

2-[4-chloro-2-fluoro-5-(pyridin-2-yl-methoxy)phenyl]-4,5,6,7-tetrahydroisobenzindole of the formula:

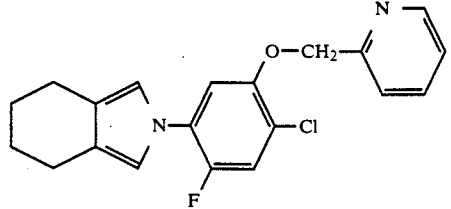

8. A compound according to claim 1, wherein such compound is
2-[4-chloro-2-fluoro-5-(isoxazol-3-yl-methoxy)phenyl]-4,5,6,7-tetrahydroisobenzindole of the formula:

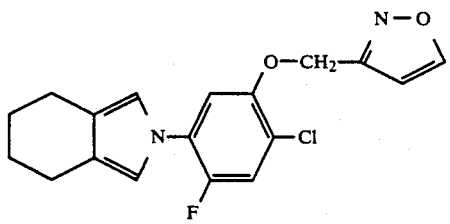

9. A herbicidal composition comprising a herbicidally effective amount of a compound according to claim 1 and a diluent.

10. A method of combating unwanted vegetation which comprises applying to such vegetation or to a locus from which is it desired to exclude such vegetation a herbicidally effective amount of a compound according to claim 1.

11. The method according to claim 10, wherein such compound is
2-(4-chloro-2-fluoro-5-propargyloxyphenyl)-4,5,6,7-tetrahydroisobenzindole,
3,4-dimethyl-1-(4-chloro-2-fluoro-5-propargyloxyphenyl)-pyrrole,
2-(5-allyloxy-4-chloro-2-fluorophenyl)-4,5,6,7-tetrahydroisobenzindole,
2-[4-chloro-2-fluoro-5-(pyridin-2-yl-methoxy)phenyl]-4,5,6,7-tetrahydroisobenzindole, or
2-[4-chloro-2-fluoro-5-(isoxazol-3-yl-methoxy)phenyl]-4,5,6,7-tetrahydroisobenzindole.

* * * * *